US012761137B2

(12) United States Patent
Kleinemolen et al.

(10) Patent No.: US 12,761,137 B2
(45) Date of Patent: Oct. 13, 2026

(54) DEVICES WITH OPTICALLY READABLE LIQUID RESERVOIRS

(71) Applicant: Truvian Sciences, Inc., San Diego, CA (US)

(72) Inventors: Ian Kleinemolen, San Diego, CA (US); Jeffrey A. Hawkins, San Marcos, CA (US); Dena Marrinucci, San Diego, CA (US); Kameel Michael Abi-Samra, Carlsbad, CA (US)

(73) Assignee: Truvian Sciences, Inc., San Diego, CA (US)

( * ) Notice: Subject to any disclaimer, the term of this patent is extended or adjusted under 35 U.S.C. 154(b) by 0 days.

(21) Appl. No.: 18/614,181

(22) Filed: Mar. 22, 2024

(65) Prior Publication Data

US 2024/0264072 A1 Aug. 8, 2024

Related U.S. Application Data

(63) Continuation of application No. 16/516,001, filed on Jul. 18, 2019, now abandoned.
(Continued)

(51) Int. Cl.
*G01N 21/03* (2006.01)
*B01L 3/00* (2006.01)
(Continued)

(52) U.S. Cl.
CPC .......... *G01N 21/0303* (2013.01); *B01L 3/502* (2013.01); *B01L 3/502715* (2013.01);
(Continued)

(58) Field of Classification Search
None
See application file for complete search history.

(56) References Cited

U.S. PATENT DOCUMENTS 4,042,462 A 8/1977 Johnson et al.
4,226,531 A 10/1980 Tiffany et al.
(Continued)

FOREIGN PATENT DOCUMENTS

CN 1206832 A 2/1999
CN 201298019 Y 8/2009
(Continued)

OTHER PUBLICATIONS

US 7,833,478 B2, 11/2010, Andersson (withdrawn)
(Continued)

*Primary Examiner* — Henry H Nguyen
(74) *Attorney, Agent, or Firm* — Snell & Wilmer, L.L.P.; April Wurster

(57) ABSTRACT

A device includes a lower reservoir surface, an upper reservoir surface, and a reservoir sidewall extending between the upper and lower reservoir surfaces which together define a reservoir. The reservoir is configured to be completely filled by a liquid such that the liquid forms a column contacting the upper reservoir surface, the lower reservoir surface, and the reservoir sidewall, with a meniscus of the liquid being outside of the reservoir. At least one of the upper reservoir surface and the lower reservoir surface is configured to transmit light.

15 Claims, 8 Drawing Sheets

Related U.S. Application Data

(60) Provisional application No. 62/722,029, filed on Aug. 23, 2018.

(51) Int. Cl.

| | |
|---|---|
| ***G01N 21/07*** | (2006.01) |
| ***G01N 21/76*** | (2006.01) |
| ***G01N 33/02*** | (2006.01) |
| ***G01N 33/15*** | (2006.01) |
| ***G01N 33/18*** | (2006.01) |
| ***G01N 33/49*** | (2006.01) |
| ***G01N 33/493*** | (2006.01) |

(52) U.S. Cl.

CPC ............ *G01N 21/07* (2013.01); *G01N 21/76* (2013.01); *G01N 33/02* (2013.01); *G01N 33/15* (2013.01); *G01N 33/1893* (2013.01); *G01N 33/4915* (2013.01); *G01N 33/493* (2013.01); *B01L 3/50273* (2013.01); *B01L 3/5085* (2013.01); *B01L 2300/0663* (2013.01); *B01L 2300/0858* (2013.01); *B01L 2300/0861* (2013.01); *B01L 2300/087* (2013.01); *B01L 2400/0409* (2013.01); *G01N 2021/0325* (2013.01)

(56) References Cited

U.S. PATENT DOCUMENTS

| | | | | |
|---|---|---|---|---|
| 4,469,793 | A | 9/1984 | Guigan | |
| 4,562,570 | A | 12/1985 | Denton | |
| 4,652,137 | A | 3/1987 | Calzi | |
| 4,656,009 | A | 4/1987 | Benajam | |
| 4,788,139 | A | 11/1988 | Ryan | |
| 4,911,642 | A | 3/1990 | Knowles | |
| 4,990,075 | A | 2/1991 | Wogoman | |
| 5,186,844 | A | 2/1993 | Burd et al. | |
| D343,457 | S | 1/1994 | Stalec | |
| 5,453,359 | A | 9/1995 | Gargan | |
| D383,215 | S | 9/1997 | Levy | |
| 5,693,233 | A | 12/1997 | Schembri | |
| 5,776,563 | A | 7/1998 | Buhl | |
| 5,888,592 | A | 3/1999 | Biallas | |
| 6,006,911 | A | 12/1999 | Levy | |
| 6,062,591 | A | 5/2000 | Ruckdeschel et al. | |
| 6,143,248 | A | 11/2000 | Kellogg et al. | |
| 6,165,795 | A | 12/2000 | Mize | |
| 6,235,531 | B1 | 5/2001 | Kopf-Sill et al. | |
| 6,302,134 | B1 | 10/2001 | Kellogg et al. | |
| 6,399,361 | B2 | 6/2002 | Brotherston et al. | |
| 6,548,788 | B2 | 4/2003 | Kellogg et al. | |
| 6,563,584 | B1 | 5/2003 | Yurrino et al. | |
| 6,582,662 | B1 | 6/2003 | Kellogg et al. | |
| 6,632,399 | B1 | 10/2003 | Kellogg et al. | |
| 6,637,463 | B1 | 10/2003 | Lei et al. | |
| 6,752,961 | B2 | 6/2004 | Kopf-Sill et al. | |
| 6,811,755 | B2 | 11/2004 | McLuen et al. | |
| 6,818,435 | B2 | 11/2004 | Carvalho et al. | |
| 6,819,408 | B1 | 11/2004 | Scrivens et al. | |
| D501,678 | S | 2/2005 | Oberhardt | |
| 6,872,572 | B2 | 3/2005 | Brady et al. | |
| 6,935,638 | B2 | 8/2005 | Ivanov et al. | |
| 7,094,354 | B2 | 8/2006 | Pugia et al. | |
| 7,238,538 | B2 | 7/2007 | Freitag et al. | |
| D598,121 | S | 8/2009 | Lastella | |
| 7,736,890 | B2 | 6/2010 | Sia et al. | |
| 7,790,110 | B2 | 9/2010 | Cho et al. | |
| 7,794,849 | B2 | 9/2010 | Lu et al. | |
| 7,947,186 | B2 | 5/2011 | Soares et al. | |
| 7,991,262 | B2 | 8/2011 | Shousterman | |
| 7,998,411 | B2 | 8/2011 | Kopf-Sill et al. | |
| 8,119,393 | B2 | 2/2012 | Qinwei | |
| 8,212,227 | B2 | 7/2012 | Watanabe et al. | |
| 8,221,701 | B2 | 7/2012 | Cho et al. | |
| D672,050 | S | 12/2012 | Lee et al. | |
| 8,372,357 | B2 | 2/2013 | Andersson et al. | |
| D683,045 | S | 5/2013 | Domack | |
| 8,731,721 | B2 | 5/2014 | Heiner et al. | |
| 8,932,538 | B2 | 1/2015 | Kim et al. | |
| 8,945,914 | B1 | 2/2015 | Schaff et al. | |
| 8,962,346 | B2 | 2/2015 | Schaff et al. | |
| 8,969,070 | B2 | 3/2015 | Yoo | |
| 9,108,198 | B2 | 8/2015 | Kim et al. | |
| 9,164,091 | B2 | 10/2015 | Kim | |
| 9,176,112 | B2 | 11/2015 | Zhang et al. | |
| 9,186,668 | B1 | 11/2015 | Schaff et al. | |
| 9,186,672 | B2 | 11/2015 | Amasia et al. | |
| 9,213,040 | B2 | 12/2015 | Hwang et al. | |
| 9,244,065 | B1 | 1/2016 | Schaff et al. | |
| 9,279,818 | B2 | 3/2016 | Yoo | |
| 9,304,129 | B2 | 4/2016 | Schaff et al. | |
| 9,410,127 | B2 | 8/2016 | Kim et al. | |
| 9,421,541 | B2 | 8/2016 | Moon et al. | |
| 9,470,609 | B2 | 10/2016 | Wimberger-Friedl et al. | |
| 9,500,579 | B1 | 11/2016 | Sommer et al. | |
| 9,616,424 | B2 | 4/2017 | Lee et al. | |
| 9,624,474 | B2 | 4/2017 | Park | |
| 9,625,916 | B2 | 4/2017 | Da Fonseca et al. | |
| 9,725,792 | B2 | 8/2017 | Ludowise et al. | |
| 9,726,685 | B2 | 8/2017 | Lee et al. | |
| 9,737,889 | B2 | 8/2017 | Moon et al. | |
| 9,816,987 | B2 | 11/2017 | Mehra et al. | |
| 9,829,426 | B2 | 11/2017 | Lee et al. | |
| D838,380 | S | 1/2019 | Self et al. | |
| 10,568,317 | B2 | 2/2020 | Deshamais et al. | |
| D936,856 | S | 11/2021 | Hawkins et al. | |
| 11,638,918 | B2 | 5/2023 | Kleinemolen et al. | |
| 2001/0048899 | A1 | 12/2001 | Marquiss | |
| 2002/0031833 | A1 | 3/2002 | Heyneker et al. | |
| 2002/0094147 | A1 | 7/2002 | Herron et al. | |
| 2002/0160170 | A1 | 10/2002 | Ishige | |
| 2003/0044992 | A1 | 3/2003 | Chao et al. | |
| 2003/0064004 | A1 | 4/2003 | Agren et al. | |
| 2003/0127609 | A1 | 7/2003 | El-Hage | |
| 2003/0161761 | A1 | 8/2003 | Williams | |
| 2003/0179378 | A1 * | 9/2003 | Lafferty | B01L 3/5085 356/440 |
| 2004/0009582 | A1 * | 1/2004 | Sandell | G01N 35/025 435/288.5 |
| 2004/0057244 | A1 | 3/2004 | Amano | |
| 2004/0120856 | A1 | 6/2004 | Andersson | |
| 2004/0139455 | A1 | 7/2004 | Ute et al. | |
| 2004/0159343 | A1 | 8/2004 | Shimbara et al. | |
| 2004/0182795 | A1 | 9/2004 | Dorian | |
| 2004/0203136 | A1 | 10/2004 | Kellogg et al. | |
| 2005/0003939 | A1 | 1/2005 | Womer et al. | |
| 2005/0048575 | A1 | 3/2005 | Coassin et al. | |
| 2005/0136545 | A1 | 6/2005 | Schmid et al. | |
| 2005/0152807 | A1 | 7/2005 | Osterloh et al. | |
| 2005/0229696 | A1 | 10/2005 | Takayama | |
| 2005/0272142 | A1 | 12/2005 | Horita | |
| 2006/0060781 | A1 | 3/2006 | Watanabe et al. | |
| 2006/0160210 | A1 | 7/2006 | Mori et al. | |
| 2006/0223166 | A1 | 10/2006 | Wilding et al. | |
| 2006/0257992 | A1 | 11/2006 | McDevitt et al. | |
| 2007/0010007 | A1 | 1/2007 | Aysta et al. | |
| 2007/0166835 | A1 | 7/2007 | Bobrow et al. | |
| 2007/0190525 | A1 | 8/2007 | Gu et al. | |
| 2007/0298433 | A1 | 12/2007 | Sia et al. | |
| 2009/0123958 | A1 * | 5/2009 | Carmon | B01F 35/71791 435/288.3 |
| 2009/0186357 | A1 | 7/2009 | Mauk et al. | |
| 2009/0202848 | A1 | 8/2009 | Lu | |
| 2009/0298092 | A1 | 12/2009 | Tsai et al. | |
| 2009/0298116 | A1 | 12/2009 | Fang | |
| 2010/0055766 | A1 | 3/2010 | Hwang et al. | |
| 2010/0081213 | A1 | 4/2010 | Lee et al. | |
| 2010/0193686 | A1 | 8/2010 | Watanabe et al. | |
| 2011/0038767 | A1 | 2/2011 | Baril | |
| 2011/0086778 | A1 | 4/2011 | Hermann | |
| 2011/0151435 | A1 | 6/2011 | Mehra et al. | |
| 2011/0152202 | A1 | 6/2011 | Du Clos | |

(56) References Cited

U.S. PATENT DOCUMENTS

| | | | | |
|---|---|---|---|---|
| 2011/0180407 | A1* | 7/2011 | Tyrrell | G01N 27/4476 204/600 |
| 2011/0189701 | A1 | 8/2011 | Kim | |
| 2011/0269151 | A1 | 11/2011 | Kim | |
| 2011/0293488 | A1 | 12/2011 | Nichols | |
| 2011/0312015 | A1 | 12/2011 | Velaskar | |
| 2012/0041315 | A1 | 2/2012 | Mycek et al. | |
| 2012/0142089 | A1 | 6/2012 | Park | |
| 2012/0200856 | A1 | 8/2012 | Bae | |
| 2012/0202673 | A1 | 8/2012 | Runyon et al. | |
| 2012/0208013 | A1 | 8/2012 | Clapper | |
| 2012/0225446 | A1 | 9/2012 | Wimberger-Friedl et al. | |
| 2013/0002753 | A1 | 1/2013 | Wang et al. | |
| 2013/0118581 | A1 | 5/2013 | Zhou | |
| 2013/0203634 | A1 | 8/2013 | Jovanovich | |
| 2013/0224568 | A1 | 8/2013 | Fukunago et al. | |
| 2013/0273584 | A1 | 10/2013 | Masci | |
| 2014/0017806 | A1 | 1/2014 | Lee | |
| 2014/0138260 | A1 | 5/2014 | Briman | |
| 2014/0185031 | A1 | 7/2014 | Zhang et al. | |
| 2014/0287524 | A1 | 9/2014 | Lee et al. | |
| 2014/0319379 | A1 | 10/2014 | Manian | |
| 2014/0341788 | A1 | 11/2014 | Kim et al. | |
| 2015/0011020 | A1* | 1/2015 | Sundvor | G01N 33/5308 422/417 |
| 2015/0064774 | A1 | 3/2015 | Moon et al. | |
| 2015/0079655 | A1 | 3/2015 | Laugharn | |
| 2015/0090674 | A1 | 4/2015 | Lee et al. | |
| 2015/0132753 | A1 | 5/2015 | Ye et al. | |
| 2015/0226652 | A1 | 8/2015 | Jayavanth et al. | |
| 2015/0293097 | A1 | 10/2015 | Godec et al. | |
| 2015/0307927 | A1* | 10/2015 | Nobile | B01L 3/502715 435/287.2 |
| 2015/0321192 | A1 | 11/2015 | Lee | |
| 2015/0338164 | A1 | 11/2015 | Day | |
| 2015/0360225 | A1 | 12/2015 | Schaff et al. | |
| 2015/0362509 | A1 | 12/2015 | Woodworth | |
| 2016/0038939 | A1 | 2/2016 | Min et al. | |
| 2016/0038940 | A1 | 2/2016 | Babcock | |
| 2016/0040213 | A1 | 2/2016 | Ludowise et al. | |
| 2016/0069919 | A1 | 3/2016 | Holmes | |
| 2016/0279640 | A1 | 9/2016 | Iqbal | |
| 2016/0369323 | A1 | 12/2016 | Revilla | |
| 2017/0023446 | A1 | 1/2017 | Rietveld et al. | |
| 2017/0067871 | A1 | 3/2017 | DeLouise et al. | |
| 2017/0080416 | A1 | 3/2017 | Panetz | |
| 2017/0108494 | A1 | 4/2017 | Mehra et al. | |
| 2017/0120259 | A1 | 5/2017 | Takeuchi | |
| 2017/0151559 | A1 | 6/2017 | Da Fonseca et al. | |
| 2017/0176306 | A1 | 6/2017 | Boehm et al. | |
| 2017/0176481 | A1 | 6/2017 | Accurso | |
| 2017/0304826 | A1 | 10/2017 | Lee et al. | |
| 2017/0354970 | A1 | 12/2017 | Reis et al. | |
| 2018/0038853 | A1 | 2/2018 | Mehra et al. | |
| 2018/0154353 | A1 | 6/2018 | Glezer et al. | |
| 2018/0161772 | A1* | 6/2018 | Rammohan | G01N 33/54313 |
| 2018/0352806 | A1 | 12/2018 | Desharnais et al. | |
| 2019/0086324 | A1 | 3/2019 | Marrinucci et al. | |
| 2019/0162670 | A1 | 5/2019 | Nose et al. | |
| 2019/0300948 | A1 | 10/2019 | Cuppens | |
| 2019/0314813 | A1 | 10/2019 | Doolan | |
| 2019/0388596 | A1 | 12/2019 | Camisani | |
| 2020/0064254 | A1 | 2/2020 | Vanderklein et al. | |
| 2020/0065959 | A1 | 2/2020 | Shartle et al. | |

FOREIGN PATENT DOCUMENTS

| | | | |
|---|---|---|---|
| CN | 1664543 | B | 12/2014 |
| CN | 110531065 | A | 12/2019 |
| DE | 19858443 | A1 | 7/2000 |
| EP | 163063 | A2 | 12/1985 |
| EP | 1542010 | A1 | 6/2005 |
| EP | 2116305 | A1 | 11/2009 |
| GB | 2387642 | A | 10/2003 |
| GB | 2542329 | A | 3/2017 |
| JP | 2000011507 | A | 1/2000 |
| JP | 2003100001 | A | 4/2003 |
| JP | 2013223441 | A | 10/2013 |
| JP | 6016168 | B2 | 10/2016 |
| WO | 1995033986 | A1 | 12/1995 |
| WO | 1999037819 | A2 | 7/1999 |
| WO | 2005083423 | A2 | 9/2005 |
| WO | 2005119211 | A1 | 12/2005 |
| WO | 2009093838 | A9 | 7/2009 |
| WO | 2011084697 | A2 | 7/2011 |
| WO | 2011093602 | A2 | 8/2011 |
| WO | 2011160015 | A2 | 12/2011 |
| WO | 2013188574 | A2 | 12/2013 |
| WO | 2014010927 | A1 | 1/2014 |
| WO | 2014172235 | A1 | 10/2014 |
| WO | 2016204638 | A2 | 12/2016 |
| WO | 2016204638 | A3 | 2/2017 |
| WO | 2017027384 | A1 | 2/2017 |
| WO | 2017103029 | A1 | 6/2017 |
| WO | 2017165630 | A1 | 9/2017 |
| WO | 2017190192 | A1 | 11/2017 |
| WO | 2017212031 | A1 | 12/2017 |
| WO | 2018005464 | A1 | 1/2018 |
| WO | 2018053217 | A | 3/2018 |
| WO | 2018117268 | A1 | 6/2018 |
| WO | 2018145005 | A1 | 8/2018 |
| WO | 2019202167 | A1 | 10/2019 |
| WO | 2020040945 | | 2/2020 |
| WO | 2020040946 | A1 | 2/2020 |

OTHER PUBLICATIONS

CA: Notice of Allowance in Canadian Applicaton No. 3110308 dated May 24, 2024.

CN: Office Action in Chinese Application No. 201980060713.8 dated Mar. 2, 2022 (20 pages) with English Translation.

CN: Office Action in Chinese Application No. 201980060713.8 dated Sep. 22, 2022 (24 pages) with English Translation.

EP: Examination Report issued in European Application No. EP19752798.9 dated Aug. 14, 2023 (6 pages).

Hawkins, "Rethinking the Clinical Laboratory Test Value Chain: Using New Technologies and New Approaches to Lower Costs, Speed Time-to-Answer, and Contribute to Improved Patient Outcomes," Truvian Slide Deck pp. 1-19 (Apr. 27, 2021).

MX: First Office Action in MX Application No. MX/a/2021/002117 dated Jul. 24, 2024 (English Translation).

Theranos' Elizabeth Holmes Speaks at AACC Meeting. "Theranos Science & Technology: The Miniaturization of Laboratory Testing," American Association for Clinical Chemistry [Video] [Screen captures from video retrieved on the Internet at URL: https://www.mpo-mag.com/contents/view_videos/2016-08-02/theranos-elizabeth-holmes-speaks-at-aacc-meeting/] pp. 1-6 (Aug. 2, 2016).

Unico "PowerSpin™ DX Centrifuge" (2015).

WO: International Search Report and Written Opinion for PCT/US2019/044038 dated Oct. 11, 2019.

"Red Blood Cell," Wikipedia (Retrieved from the Internet on Jun. 11, 2020 at https://en.wikipedia.org/wiki/Red_blood_cell) (1987), p. 4.

Bond et al., "Drop-to-Drop Variations in the Cellular Components of Fingerprick Blood," Am. J. Clin. Pathol. 144, pp. 885-894 (2015).

EP: Examination Report issued in European Application No. EP19752798.9 dated Dec. 5, 2024 (4 pages).

Gale et al., "A review of current Methods in Microfluidic device fabrications and Future commercialization prospects," 3(60): pp. 1-25 (2018).

Giroux et al., "Influence of calcium ions in the flow cytometric analysis of human CD8-positive cells," 62A(1):61-64 (Nov. 2004) https://doi.org/10.1002/cyto.a.20084.

Hauke et al., "An Improved Design and Versatile New Lamination Fabrication Method for Twin Electrode Thin Layer Cells Utilizing Track-etch Membranes", Electroanalysis, VHC Publishers, Inc, US, 31(1) (2018): pp. 58-65 XP071939736, ISSN: 1040-0397, DOI: 10.1002/ELAN.201800539.

(56) References Cited

OTHER PUBLICATIONS

Kartell Microscope Slide Tray. Online, published date unknown. Retrieved on Jan. 28, 2025 from URL: https://www.dynalon.com/PublicStore/producUKartelI-Microscope-Slide-Tray,274,314.aspx.
Kratz et al., "Characterization of four functional biocompatible pressure-sensitive adhesives for rapid prototyping of cell-based lab-on-a-chip and organ-on-a-chip systems," Scientific Reports 9(1), 9287 (2019) https://doi.org/10.1038/s41598-019-45633-x.
Lassale et al., "Elements of the complete blood count associated with cardiovascular disease incidence: Findings from the EPIC-NL cohort study," Scientific Reports (2018) 8:3290.
Li et al., "Out-of-plane microvalves for whole blood separation on lab-on-a-CD;Out-of-plane microvalves for whole blood separation on lab-on-a-CD", Journal of Micromechanics & Microengineering, Institute of Physics Publishing, Bristol, GB, vol. {0} 20, No. {0} 10, Sep. 29, 2010 (Sep. 29, 2010), p. 105024, XP020198610 DOI: 10.1088/0960-1317/20/10/105024.
Olanrewaju et al., "Capillary microfluidics in microchannels: from microfluidic networks to capillaric circuits", Lab on a Chip, 18, pp. 2315-2478 (2018) Available on the Internet at URL: https://pubs.rsc.org/en/content/articlelanding/2018/1c/c81c00458g.
Steigert et al., "Integrated siphon-based metering and sedimentation of whole blood on a hydrophilic lab-on-a-disk", Biomedical Microdevices, Kluwer Academic Publishers, BO,vol. {0} 9, No. {0} 5, May 16, 2007 (May 16, 2007), p. 675-679, XP019524286 DOI: 10.1007/S10544-007-9076-0 external link.
Wörner et al., "Platelet aggregation and the release induced by inophores for divalent cations," Thrombosis Research 6(4):295-305 (1975).
Zhang et al., "A simple statistical parameter for use in evaluation and validation of high throughput screening assays" Journal of Biomolecular Screening 4:67-73 (1999).

* cited by examiner

DEVICES WITH OPTICALLY READABLE LIQUID RESERVOIRS

RELATED APPLICATIONS

This application is a continuation application of U.S. patent application Ser. No. 16/516,001 filed on Jul. 18, 2019, which claims benefit of U.S. Patent Application No. 62/722,029 filed on Aug. 23, 2018, the contents of which are hereby fully incorporated by reference.

FIELD

This application relates to devices with liquid reservoirs.

BACKGROUND

It can be useful to read out information optically from liquid samples, for example by shining laser light into a liquid sample and sensing light from the liquid sample, wherein information about the sample can be determined from the sensed light.

SUMMARY

Devices with optically readable liquid reservoirs, and methods of making and using the same, are provided herein.

In a first aspect, a device includes a lower reservoir surface, an upper reservoir surface, and a reservoir sidewall extending between the upper and lower reservoir surfaces which together define a reservoir. The reservoir is configured to be completely filled by a liquid such that the liquid forms a column contacting the upper reservoir surface, the lower reservoir surface, and the reservoir sidewall, with a meniscus of the liquid being outside of the reservoir. At least one of the upper reservoir surface and the lower reservoir surface is configured to transmit light.

A channel can be coupled to the reservoir sidewall. With such an arrangement, the meniscus can be located within the channel. A well fluidically can be coupled to the reservoir via the channel such that the meniscus is located within the well.

An assay chamber fluidically can be coupled to the reservoir via the channel. The assay chamber can include an inlet. The assay chamber can have a reagent disposed therein. The reagent can be configured to react with liquid received in the assay chamber via the inlet. The channel can be configured to transmit the liquid from the assay chamber to the reservoir responsive to application of a force (e.g., centrifugal force, a gas source, etc.) to the assay chamber.

A rotatable disc can be provided in which the reservoir is disposed. Rotating such disc can generate centrifugal force.

The assay chamber can include a lower assay chamber surface, an upper assay chamber surface, and an assay chamber sidewall extending between the upper and lower assay chamber surfaces. The assay chamber sidewall can include a first portion extending substantially perpendicularly to the upper and lower assay chamber surfaces. The assay chamber sidewall can include a second portion extending at an angle (e.g., an obtuse angle, etc.) from the lower assay chamber surface.

The liquid can be conveyed upward along the second portion and into the channel responsive to application of force.

In some variations, the assay chamber sidewall and the reservoir sidewall can be integrally formed with one another. In other variations, the upper assay chamber surface and the upper reservoir surface can be integrally formed with one another and attached to the integrally formed assay chamber sidewall and the reservoir sidewall. In still other variations, the lower assay chamber surface and the lower reservoir surface can be integrally formed with one another and attached to the integrally formed assay chamber sidewall and the reservoir sidewall. In further variations, all of the assay chamber sidewall, the channel, and the reservoir sidewall can be integrally formed with one another.

Further, the assay chamber sidewall and the reservoir sidewall can be discrete elements. The upper assay chamber surface and the upper reservoir surface can be discrete elements. The lower assay chamber surface and the lower reservoir surface can be discrete elements. The assay chamber sidewall, the channel, and the reservoir sidewall can be discrete elements.

The channel and the sidewall can be integrally formed with one another. The channel and the sidewall can be discrete elements.

The lower reservoir surface, the upper reservoir surface, and the sidewall can be discrete elements attached to one another.

The reservoir sidewall can define a circular, rectangular, square, or irregular cross section of the reservoir.

The device can include a source of light such as, for example, a laser, light emitting diode, or lamp. The source of the light can be positioned over the upper reservoir surface and configured to transmit the light through (e.g., laterally through, etc.) the upper reservoir surface. The source of the light further can be configured to transmit the light through the column and then through the lower reservoir surface. The source of the light can be positioned under the lower reservoir surface and be configured to transmit the light through the lower reservoir surface. The source of the light further can be configured to transmit the light through the column and then through the upper reservoir surface.

The device can include a sensor configured to receive (and characterize) the light transmitted through the at least one of the upper reservoir surface and the lower reservoir surface. The sensor can be positioned in a variety of locations. For example, the sensor can be positioned over the upper reservoir surface and be configured to receive the light through the upper reservoir surface. The sensor can be positioned under the lower reservoir surface and be configured to receive the light through the lower reservoir surface.

The light can be generated by, for example, fluorescence or chemiluminescence.

Reagents that can be used with the device include an antibody, enzyme, or particle.

The reservoir can have varying volumes. For example, the reservoir can have a volume of about 1-200 μL, or about 10-100 μL, or about 15-50 μL, or about 10-30 μL, or about 5-20 μL.

The device can house or otherwise characterize a wide variety of liquids. For example, the liquid can be a bodily fluid such as whole blood, blood plasma, blood cells, urine, and/or spit. The liquid can be a food sample, a water sample, a purified nucleic acid, a pharmaceutical compound, a buffer, and/or a reagent.

In another aspect, a reservoir can be filled (e.g., completely filled, substantially filled, etc.) with a liquid. The reservoir can include a lower reservoir surface, an upper reservoir surface, and a reservoir sidewall extending between the upper and lower reservoir surfaces. The liquid forms a column contacting the upper reservoir surface, the lower reservoir surface, and the reservoir sidewall. A meniscus of the liquid is located outside of the reservoir. Light is transmitted through at least one the upper reservoir surface and the lower reservoir surface.

DETAILED DESCRIPTION

Devices with optically readable liquid reservoirs, and methods of making and using the same, are provided herein. The present devices can facilitate obtaining information from liquid samples by providing a reservoir that can be completely filled with liquid such that a meniscus of the liquid is outside of the reservoir. Location of the meniscus outside of the reservoir can facilitate reading out information optically from the sample within that reservoir. For example, the liquid can form a column within the reservoir that is bounded by top and bottom surfaces and a sidewall of the reservoir. At least one of top and bottom surfaces is at least partially transparent, thus permitting sensing of light from or through the liquid and through the partially transparent top and/or bottom surface(s) without that light being transmitted through the meniscus. As a comparison, transmission of such light through a meniscus can alter the path focus, and other qualities of the light, which can hinder read out of information.

Figure 1A:
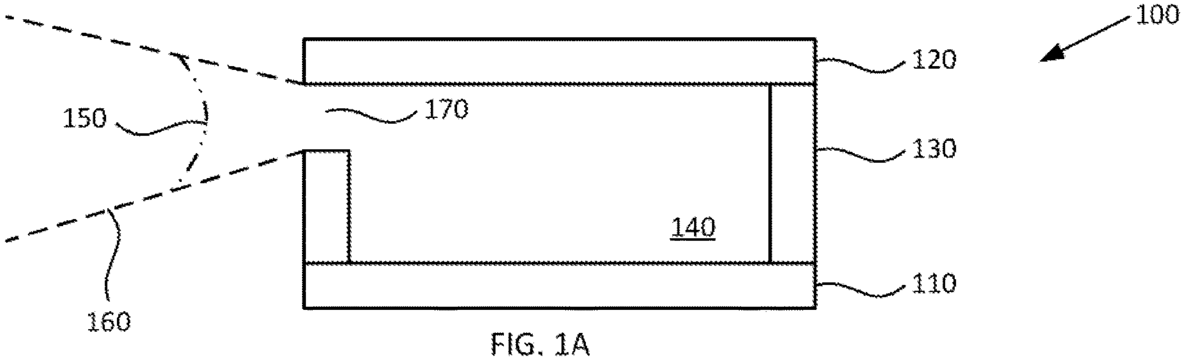
FIGS. 1A-1B respectively schematically illustrate cross-sectional and plan views of an exemplary device with an optically readable liquid reservoir, according to various configurations provided herein.
Figure 1B:
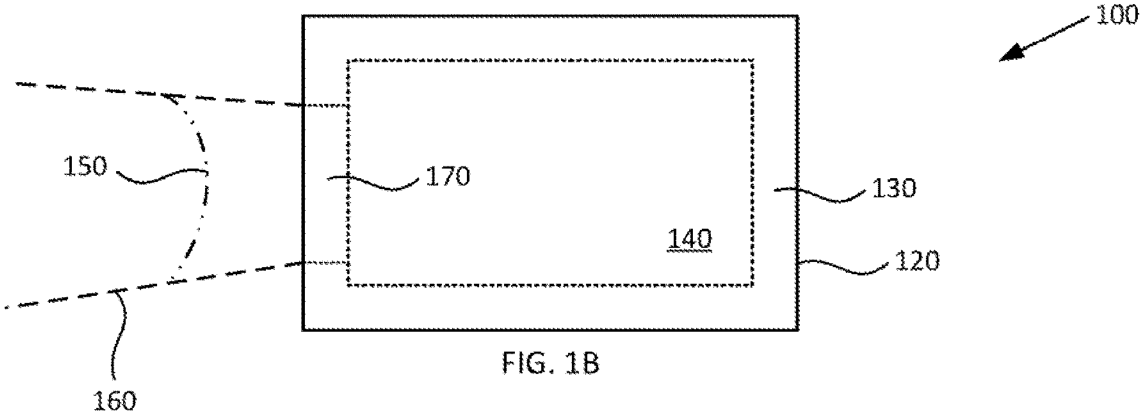

FIGS. 1A-1B respectively schematically illustrate cross-sectional and plan views of an exemplary device with an optically readable liquid reservoir, according to various configurations provided herein. In FIGS. 1A-1B, device 100 includes lower reservoir surface 110, upper reservoir surface 120, and one or more reservoir sidewalls 130 extending between the upper and lower reservoir surfaces 110. Lower reservoir surface 110, upper reservoir surface 120, and reservoir sidewall(s) 130 define reservoir 140. As shown in FIGS. 1A-1B, reservoir 140 is configured to be completely filled by a liquid such that the liquid forms a column contacting upper reservoir surface 120, lower reservoir surface 110, and reservoir sidewall 130, with a meniscus 150 of the liquid being outside of the reservoir. By "completely filled" it is meant that the liquid contacts substantially the entirety of reservoir 140, e.g., substantially completely and directly contacts upper surface 120, substantially completely and directly contacts lower surface 110, and substantially completely and directly contacts sidewall(s) 130. Such substantially complete and direct contact between the liquid and the surface can include a relatively small area, for example 10% or less of that surface's area, in which a bubble or particle is interposed between the liquid and that surface. Additionally, it should be appreciated that the liquid and meniscus 150 optionally need not be considered to form part of the present device 100.

In FIGS. 1A-1B, an optional structure 160 is fluidically coupled to reservoir 140, e.g., via an opening 170 through sidewall(s) 130, and configured to receive meniscus 150. In FIG. 1B, the boundary of reservoir 140 and opening 170 are indicated in dotted lines. It should be appreciated that structure 160 can be, but need not necessarily be considered to form part of the present device 100. Structure 160 can have any suitable configuration for receiving meniscus 150, for example but not limited to examples such as described in greater herein with reference to FIGS. 3A-3B and 5A-5C.

In configurations such as illustrated in FIGS. 1A-1B, at least one of the upper reservoir surface 120 and lower reservoir surface 110 is configured to transmit light. As such, light from or through the top and/or bottom of the column of liquid within reservoir 140 can be sensed from outside of the reservoir so as to obtain information about that liquid. For example, FIGS. 2A-2C schematically illustrate cross-sectional views of exemplary devices with an optically readable liquid reservoir, a light sensor, and an optional light source, according to various configurations provided herein.

In the exemplary configuration illustrated in FIG. 2A, device 200 includes lower reservoir surface 210, upper reservoir surface 220, and reservoir sidewall(s) 230 defining a reservoir 240 configured similarly as described with reference to FIGS. 1A-1B. Device 200 optionally also can include source 280 of light, which can be configured so as to transmit light into reservoir 240 via the upper reservoir surface 220 or lower reservoir surface 210. Examples of source 280 of light include, but are limited, to a laser, light emitting diode, or lamp (such as a halogen, mercury, or xenon lamp). The light generated by source 280 can be narrowband or broadband, and can be coherent or incoherent. Additionally, the light can have any suitable wavelength(s), for example in the infrared, visible, or ultraviolet regions of the spectrum. In configurations such as illustrated in FIG. 2A, source 280 of the light optionally is positioned over upper reservoir surface 220 and configured to transmit the light through the upper reservoir surface 220. Additionally, as illustrated in FIG. 2A, source 280 of the light further optionally can be configured to transmit the light through the column of liquid within reservoir 240 and then through the lower reservoir surface 210. In such configurations, both upper reservoir surface 220 and lower reservoir surface 210 can be at least partially optically transparent. Additionally, it should be appreciated that source 280 can be located at any suitable position relative to reservoir 240. For example, in an alternative configuration, source 280 of the light optionally can be positioned under the lower reservoir surface 210 and configured to transmit the light through the lower reservoir surface 210. As a further option of such a configuration, source 280 of the light further can be configured to transmit the light through the column of liquid within reservoir 270 and then through the upper reservoir surface 220. In such configurations, both upper reservoir surface 220 and lower reservoir surface 210 can be at least partially optically transparent.

Figure 2A:
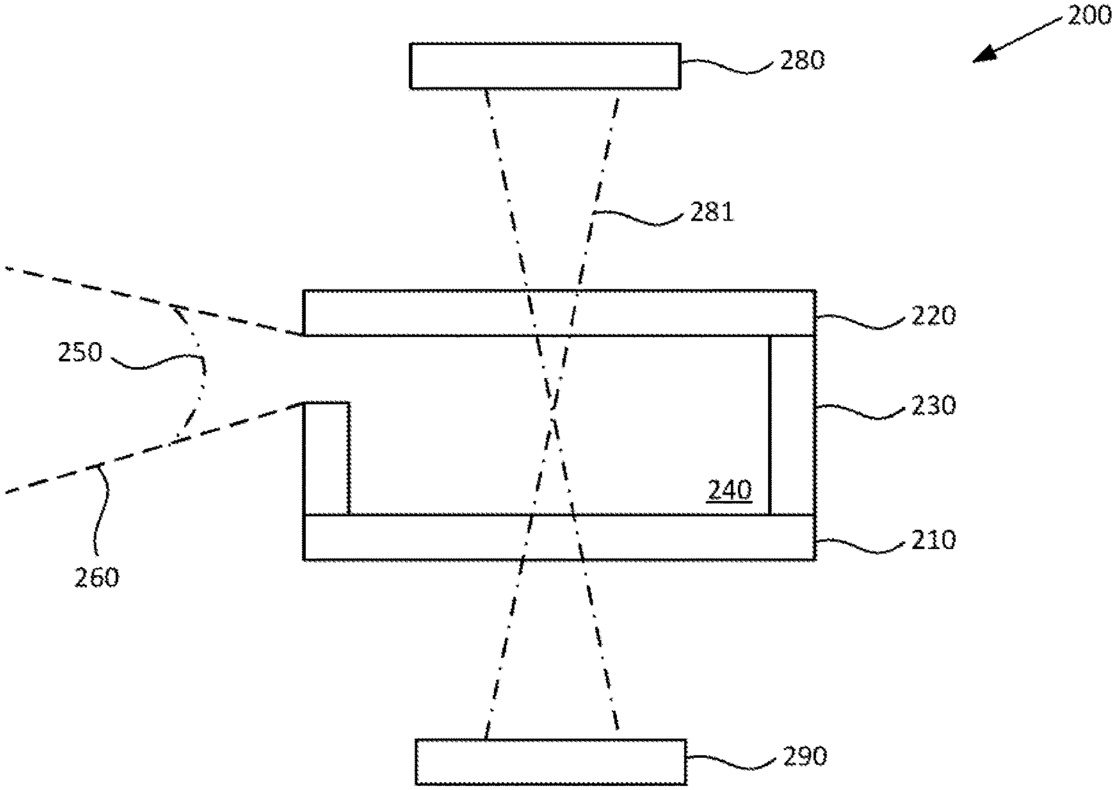
FIGS. 2A-2C schematically illustrate cross-sectional views of exemplary devices with an optically readable liquid reservoir, a light sensor, and an optional light source, according to various configurations provided herein.
Figure 2B:
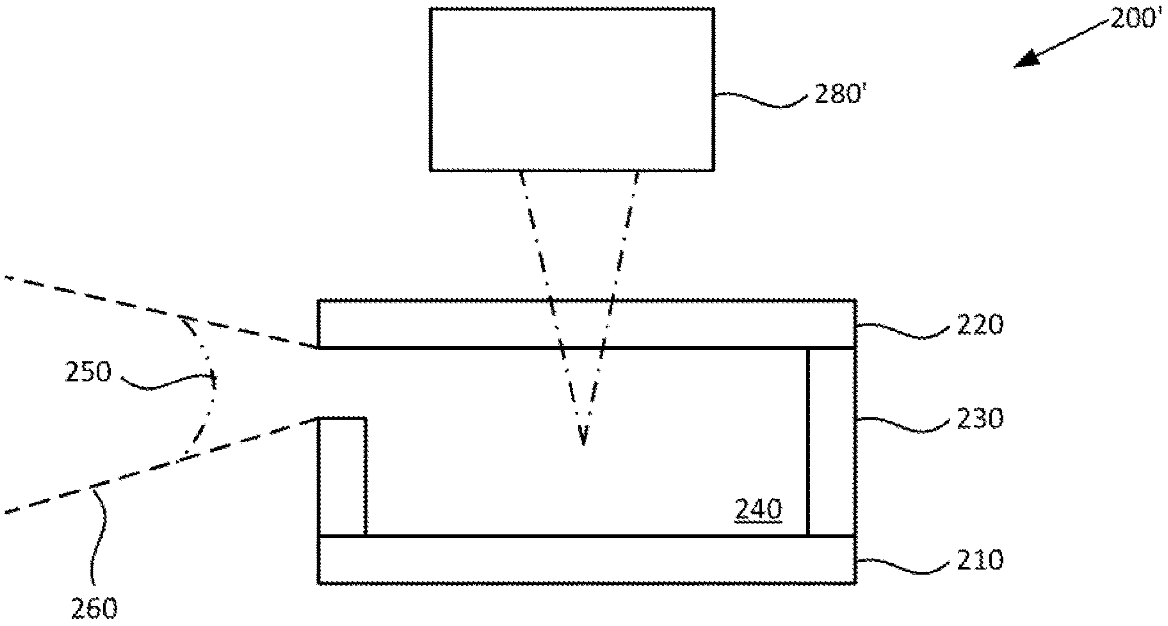
Figure 2C:
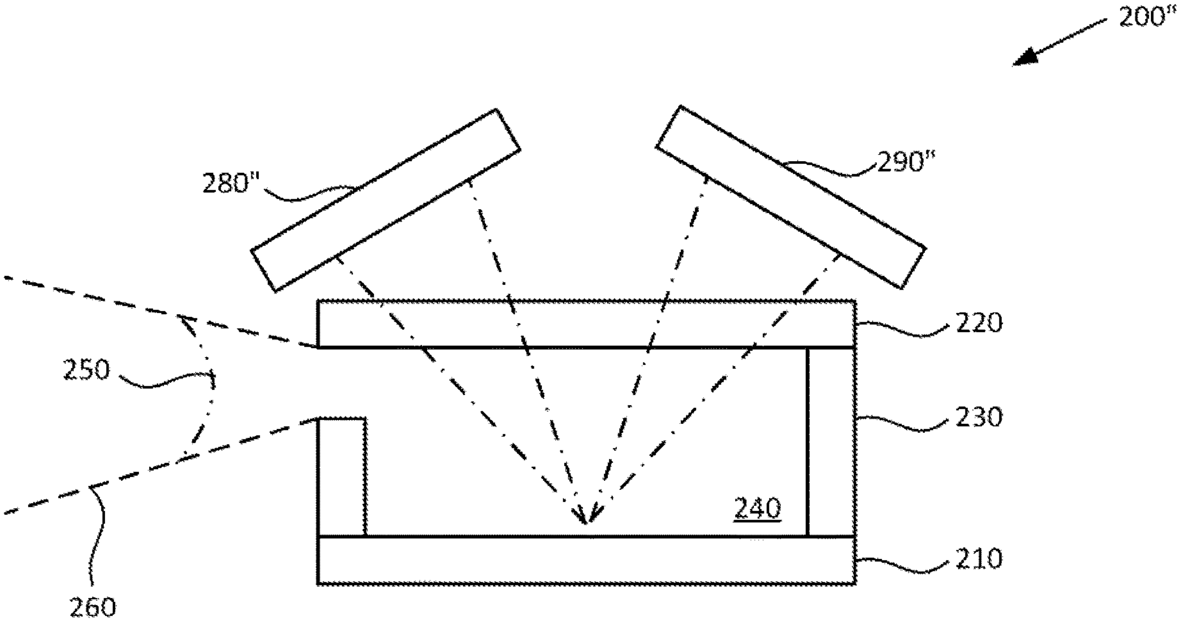

Referring still to the exemplary configuration illustrated in FIG. 2A, device 200 optionally further can include sensor 290 configured to receive the light transmitted through the upper reservoir surface 220 and/or lower reservoir surface 210. Sensor 290 can have any suitable configuration, such as a photodetector, photodiode, photomultiplier, charge coupled device, and the like, and can be configured to generate an electrical signal based on light received from or through the liquid within reservoir 240. Information about the liquid can be obtained based on such an electrical signal. For example, in FIG. 2A, sensor 290 is positioned under the lower reservoir surface 210 and is configured to receive the light through the lower reservoir surface 210, which light can be generated by source 280. In an alternative configuration such as noted above in which source 280 of the light is positioned under lower reservoir surface 210, sensor 290 optionally can be positioned over the upper reservoir surface 220 and configured to receive the light through the upper reservoir surface 220. In any such configuration, note that meniscus 250 is located outside of reservoir 240, e.g., within structure 260. As such, meniscus 250 is outside of the optical path 281 between source 280 and sensor 290 and therefore does not interfere with optically obtaining information about the liquid.

Note that information about the liquid can be obtained in a variety of suitable configurations, not all of which require "transmission-mode" arrangements of the light source and/or sensor such as described above with reference to FIG. 2A, which can be considered to be arrangements. For example, FIG. 2B illustrates an exemplary device 200' including element 280' located above upper reservoir surface 220 and configured to transmit light to and/or receive light from liquid within reservoir 240 only through upper reservoir surface 220. Alternatively, element 280' can be located below lower reservoir surface 210 and configured to transmit light to and/or receive light from liquid within reservoir 240 only through lower reservoir surface 210. For example, element 280' optionally can include a light source (which can be configured similarly as light source 280 described with reference to FIG. 2A) and/or optionally can include a sensor (which can be configured similarly as sensor 290 described with reference to FIG. 2A). In configurations where element 280' includes both a light source and a sensor, element 280' optionally can include at least one optic that both transmits light from the light source and receives light from the liquid within reservoir 240. In one exemplary configuration, element 280' is or includes a confocal microscope.

As another example, FIG. 2C illustrates an exemplary device 200" including source 280" of light and sensor 290", both of which are located above upper reservoir surface 220 and respectively configured to transmit light to and receive light from liquid within reservoir 240 only through upper reservoir surface 220. Alternatively, source 280" of light and sensor 290" both can be located below lower reservoir surface 210 and respectively configured to transmit light to and receive light from liquid within reservoir 240 only through lower reservoir surface 210. Source 280" can be configured similarly as light source 280 described with reference to FIG. 2A, and sensor 290" can be configured similarly as sensor 290 described with reference to FIG. 2A. The configuration illustrated in FIG. 2C can be considered to be a "reflection-mode" configuration.

In some configurations such as exemplified by FIGS. 2A-2C, light can be generated by a suitable light source, e.g., 280, 280', or 280" and can be received by a suitable sensor, e.g., 290, 280', or 290" which generates an electrical signal based upon which information about the liquid within reservoir 240 can be obtained. For example, the light can be partially or fully absorbed by the liquid within reservoir 240 generating an interpretable signal within the electrical signal generated by the sensor, and information about the liquid can be obtained by analyzing the electrical signal. As another example, the light can cause the liquid within reservoir to fluoresce, such fluorescence generating an interpretable signal within the electrical signal generated by the sensor, and information about the liquid can be obtained by analyzing the electrical signal. However, a light source need not necessarily be required in order to obtain information about the liquid within reservoir 240 via light that the sensor receives. For example, the light can be generated by chemiluminescence of the liquid, such chemiluminescence generating an interpretable signal within the electrical signal generated by the sensor, and information about the liquid can be obtained by analyzing the electrical signal. Other suitable configurations for obtaining and analyzing light from liquid within reservoir 240 can be implemented.

Figure 3A:
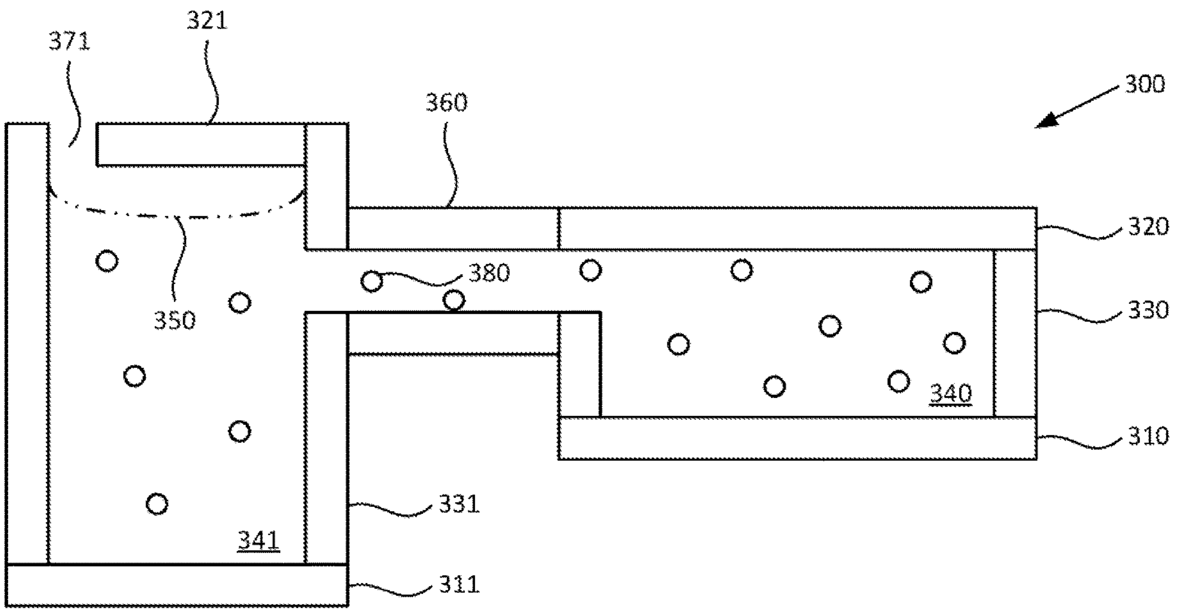
FIGS. 3A-3B schematically illustrate cross-sectional views of exemplary devices with wells attached to optically readable reservoirs, according to various configurations provided herein.
Figure 3B:
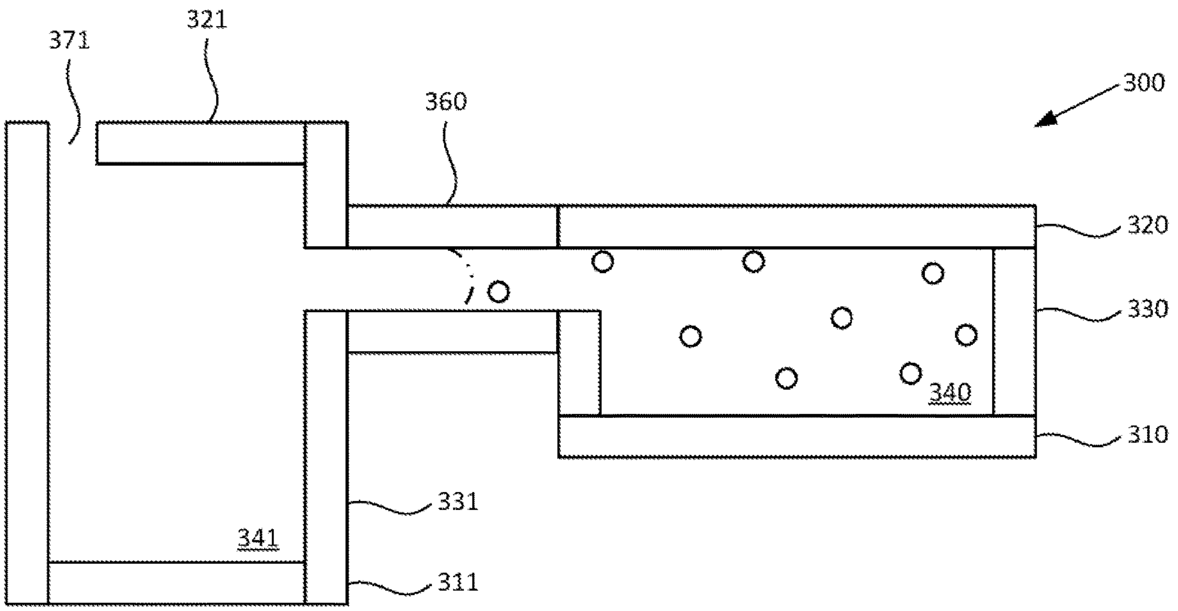

As noted above with reference to FIGS. 1A-1B, the present devices can include or be coupled to another structure 160 within which the liquid's meniscus can be located. For example, FIGS. 3A-3B schematically illustrate cross-sectional views of exemplary devices with wells attached to optically readable reservoirs, according to various configurations provided herein. In the exemplary configuration illustrated in FIGS. 3A-3B, device 300 includes lower reservoir surface 310, upper reservoir surface 320, and reservoir sidewall(s) 330 defining a reservoir 340 configured similarly as described with reference to FIGS. 1A-1B. Device 300 optionally also can include a source of light and/or sensor configured similarly as described with reference to FIGS. 2A-2C.

As illustrated in FIGS. 3A-3B, device 300 optionally can include channel 360 coupled to reservoir sidewall 330. In some configurations, device 300 optionally further includes a well 341 that is fluidically coupled to the reservoir 340 via the channel 360. The meniscus 350 can have any suitable location within device 300. For example, in some configurations such as illustrated in FIG. 3A, meniscus 350 is located within the well 341, while in other configurations such as illustrated in FIG. 3B, meniscus 350 is located within the channel 360.

Optionally, well 341 can be or include an assay chamber. By "assay chamber" it is meant a reservoir in which a liquid can be assayed, e.g., mixed with one or more reagents with which the liquid chemically and/or biologically reacts to generate a change in the liquid that can be detected optically (e.g., using a sensor such as described with reference to FIGS. 2A-2C). For example, in configurations such as illustrated in FIGS. 3A-3B, well 341 can define an assay chamber 341 that is fluidically coupled to reservoir 340 via channel 360. The assay chamber optionally can include an inlet 371, and as a further option can include a reagent 380 within the assay chamber 341. Reagent 380 can be configured to react with liquid which is received in the assay chamber 341 via the inlet 371. The reagent 380 can be dry or wet prior to addition of the liquid via inlet 371. As illustrated in FIGS. 3A-3B, reagent 380 can be dispersed throughout or dissolved in the liquid. Exemplary reagents include, but are not limited to, an antibody, enzyme, or particle. However, note that use of reagent is optional, in which case element 341 may be considered simply to be a well.

Note that liquid added into assay chamber 341 (which also can be considered a well), e.g., via inlet 371, may not necessarily flow under its own power into reservoir 340 via channel 360. In some configurations, channel 360 is configured to convey the liquid from the assay chamber to the reservoir responsive to application of a force to assay chamber 341. For example, device 300 can include a source of gas (not specifically illustrated) configured to apply the force via the gas. Such gas can be introduced to assay chamber 341 via inlet 371 and can force liquid through channel 360 and into reservoir 340 so as to completely fill the reservoir in a manner such as described with reference to FIGS. 1A-1B. In other exemplary configurations, the force can include a centrifugal force. For example, device 300 can include a rotatable disc in which reservoir 340 is disposed, wherein rotating the disc generates the centrifugal force. An exemplary rotatable disc is described herein with reference to FIG. 6.

In the nonlimiting configuration illustrated in FIGS. 3A-3B, assay chamber 341 (which also can be considered a well) can include lower assay chamber surface 311, upper assay chamber surface 321, and assay chamber sidewall(s) 331 extending between the upper and lower assay chamber surfaces 321, 311. Any suitable combination of lower assay chamber surface 311, upper assay chamber surface 321, assay chamber sidewall(s) 331, channel 360, lower reservoir surface 310, upper reservoir surface 320, and reservoir sidewall(s) 330 can be formed as discrete elements that are attached to one another, or can be integrally formed with one another, and can have any suitable shape and dimensions. In a nonlimiting example, reservoir 340 and/or well 341 each can have a volume of about 1-200 μL, or about 10-100 μL, or about 15-50 μL, or about 10-30 μL, or about 5-20 μL. As used herein, "about" means within 10% of the stated value.

Note that in configurations in which meniscus 350 is located within well 341 such as shown in FIG. 3A, the meniscus can be oriented substantially parallel to the upper and/or lower surfaces 321, 311, and can have a surface area similar to that of the lower surface 311 and/or upper surface 321 as a result of gravitational effects. In comparison, in configurations in which meniscus 350 is located within channel 360 such as shown in FIG. 3B, the meniscus can be oriented substantially perpendicularly to the length of the channel, and can have a surface area similar to that of the height and width of the channel as result of surface tension and capillary action. In such a configuration, the liquid can have a smaller meniscus and can experience a lower rate of evaporation in the configuration of FIG. 3B relative to that in the configuration of FIG. 3A.

Figure 4A:
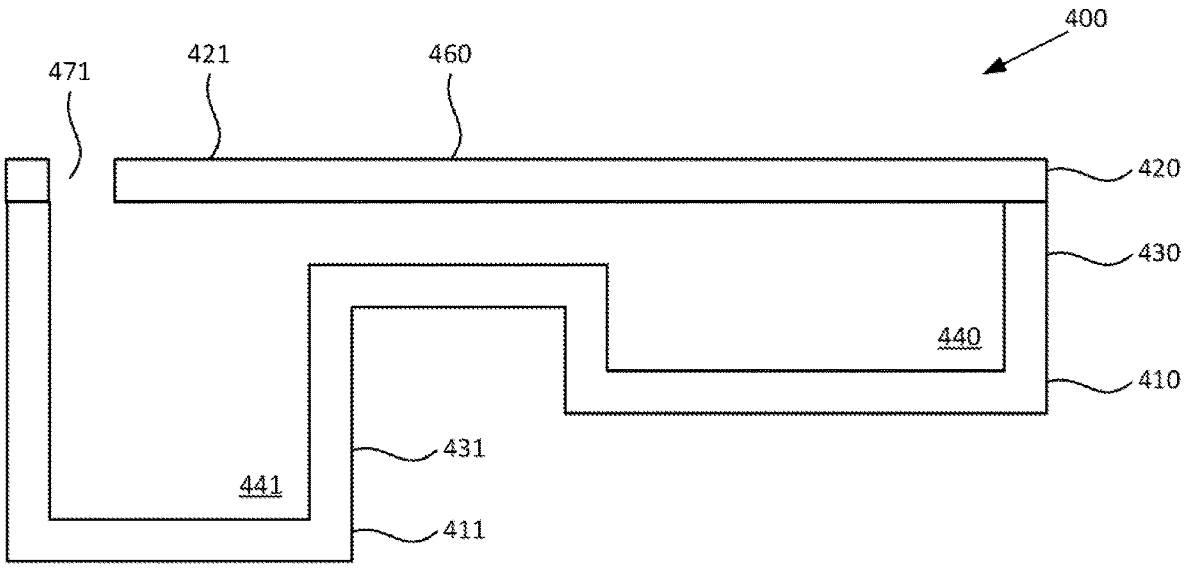
FIGS. 4A-4C schematically illustrate views of alternative devices with an optically readable liquid reservoir, according to various configurations provided herein.
Figure 4B:
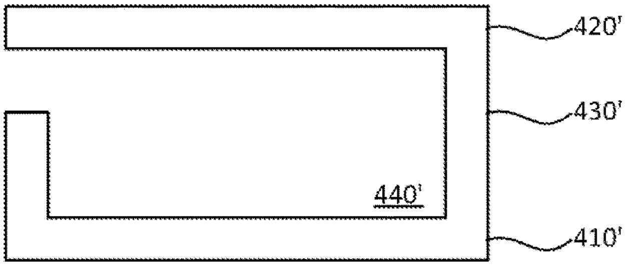
Figure 4C:
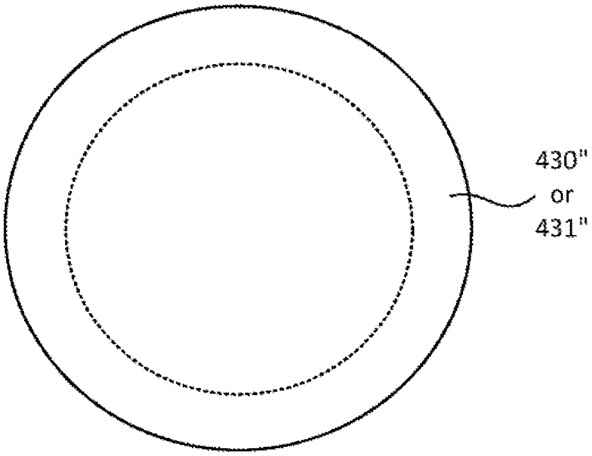

FIGS. 4A-4C schematically illustrate views of alternative devices with an optically readable liquid reservoir, according to various configurations provided herein. In the nonlimiting configuration of device 400 illustrated in FIG. 4A, lower assay chamber surface 411, assay chamber sidewall(s) 431, lower surface of channel 460, lower reservoir surface 410, and reservoir sidewall(s) 330 are integrally formed with one another, while upper assay chamber surface 421, upper surface of channel 460, and upper reservoir surface 420 are integrally formed with one another. Referring again to FIGS. 3A-3B, assay chamber sidewall(s) 331 and reservoir sidewall(s) 330 optionally can be integrally formed with one another in a manner similar to that of assay chamber sidewall(s) 431 and reservoir sidewall(s) 430, while other suitable components of device 300 can be integrally formed with one another or discrete from one another For example, the upper assay chamber surface 321 and the upper reservoir surface 320 optionally can be integrally formed with one another in a manner such as illustrated in FIG. 4A and can be attached to such an integrally formed assay chamber sidewall(s) 331 and reservoir sidewall(s) 330. As another example, lower assay chamber surface 311 and lower reservoir surface 310 can be integrally formed with one another in a manner such as illustrated in FIG. 4A and attached to such an integrally formed assay chamber sidewall(s) 331 and reservoir sidewall(s) 330. In still other examples, assay chamber sidewall 331, one or more surfaces of channel 360, and reservoir sidewall 330 can be integrally formed with one another in a manner such as illustrated in FIG. 4A. In yet other configurations, assay chamber sidewall(s) 331 and reservoir sidewall(s) 330 optionally can be discrete elements in a manner such as illustrated in FIGS. 3A-3B. As a further option, upper assay chamber surface 321 and upper reservoir surface 320 can be discrete elements and/or lower assay chamber surface 311 and lower reservoir surface 310 can be discrete elements in a manner such as illustrated in FIGS. 3A-3B. Additionally or alternatively, optionally assay chamber sidewall(s) 331, one or more surfaces of channel 360, and reservoir sidewall(s) 330 can be discrete elements in a manner such as illustrated in FIGS. 3A-3B.

Referring still to FIGS. 3A-3B, note that channel 360 and assay chamber (well) 341 each are optional. If present, such features can be integrally formed with, or discrete from, one or more features of reservoir 340 which features also can be integrally formed with, or discrete from, one another. For example, one or more surfaces (and optionally all surfaces) of optional channel 360 and sidewall 330 can be integrally formed with one another, or can be discrete elements. In the nonlimiting configuration illustrated in FIG. 4B, lower reservoir surface 410', upper reservoir surface 420', and reservoir sidewall(s) 430' are all formed integrally with one another. In another configuration, lower reservoir surface 410', upper reservoir surface 420', and sidewall(s) 430' are discrete elements attached to one another in a manner such as illustrated in FIGS. 3A-3B.

Additionally, reservoir sidewall(s) and assay chamber (well) sidewall(s) such as provided herein can have any suitable cross section. For example, the sidewall(s) of the reservoir and/or assay chamber can define a circular, rectangular, square, or irregular cross section of the reservoir and/or assay chamber. A non-limiting example such sidewall(s) defining a rectangular cross-section is illustrated in FIG. 1B, and such a cross-section similarly can be defined by the sidewall(s) of the assay chamber (well). FIG. 4C illustrates a circular cross section that can be defined by sidewall(s) of the reservoir 430" and/or assay chamber 431".

Figure 5A:
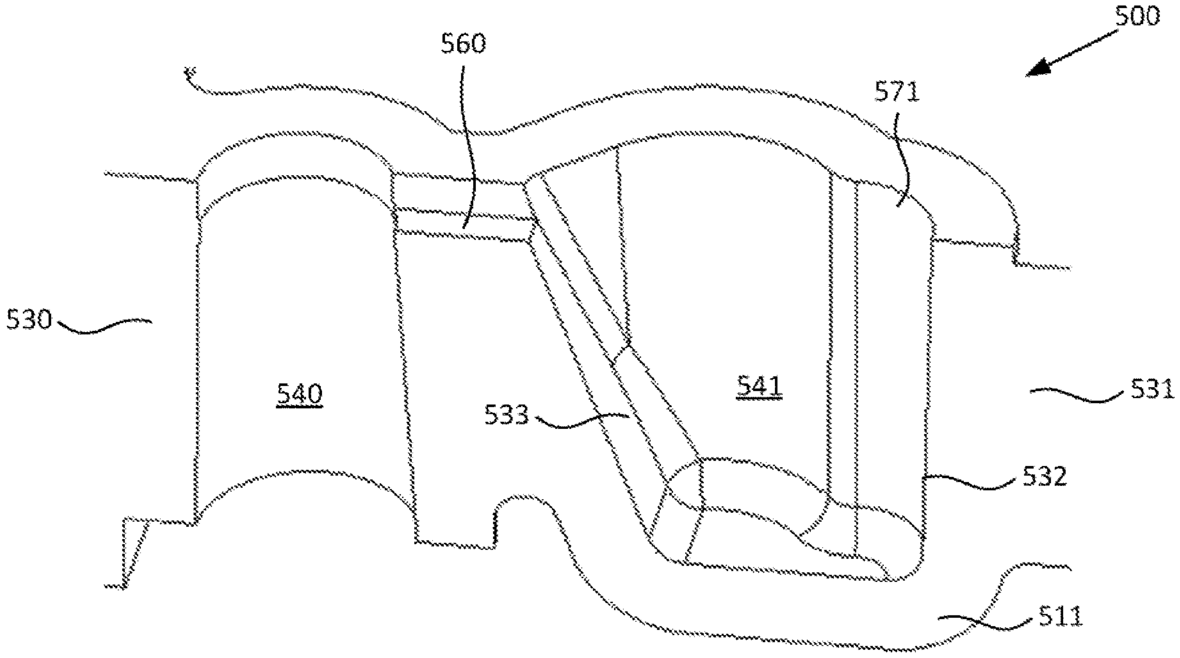
FIGS. 5A-5C schematically illustrate perspective and plan views of components of an alternative device with an optically readable liquid reservoir, according to various configurations provided herein.
Figure 5B:
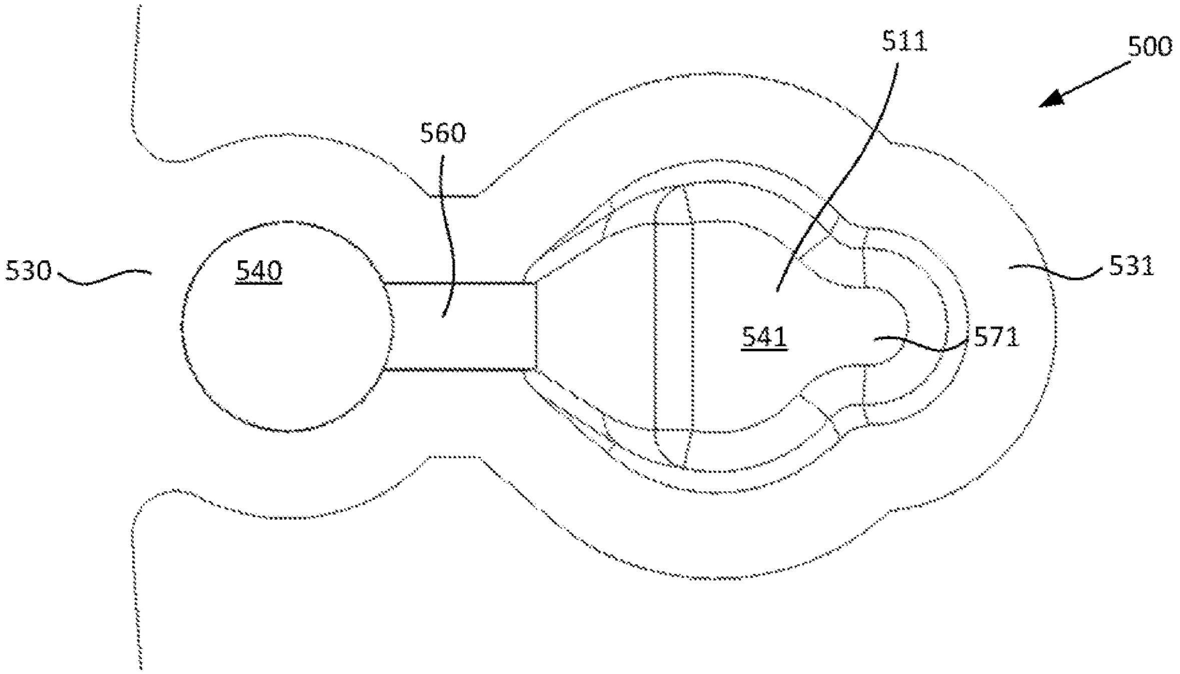
Figure 5C:
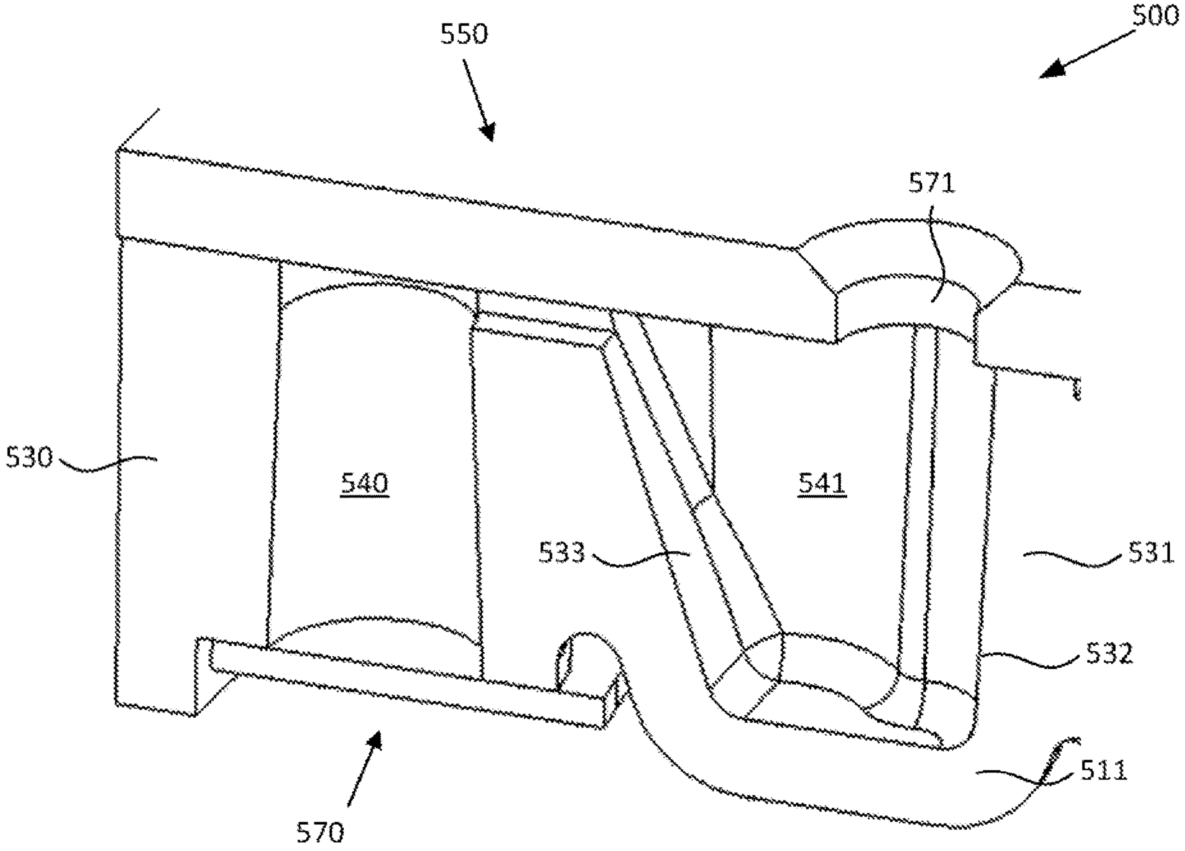

Still other variations of the present devices readily can be envisioned. For example, FIGS. 5A-5C schematically illustrate perspective and plan views of components of an alternative device 500 with an optically readable liquid reservoir, according to various configurations provided herein. In the exemplary configuration illustrated in FIGS. 5A-5C, device 500 includes a lower reservoir surface (not specifically illustrated), upper reservoir surface (not specifically illustrated), and reservoir sidewall(s) 530 defining a reservoir 540 configured similarly as described with reference to FIGS. 1A-1B. Device 500 optionally also can include a source of light and/or sensor configured similarly as described with reference to FIGS. 2A-2C.

As illustrated in FIGS. 5A-5C, device 500 optionally can include channel 560 coupled to reservoir sidewall 530. In some configurations, device 500 optionally further includes a well 541 that is fluidically coupled to the reservoir 540 via the channel 560. The meniscus (not specifically illustrated) can have any suitable location within device 500. For example, in some configurations similar to those illustrated in FIG. 3A, the meniscus is located within the well 541, while in other configurations similar to those illustrated in FIG. 3B, meniscus 350 is located within the channel. Optionally, well 541 can be or include an assay chamber configured in a manner similar to that described with reference to FIGS. 3A-3B. The assay chamber optionally can include an inlet 571, and as a further option can include a reagent (not specifically illustrated) within the assay chamber 541 which is configured to react with liquid which is received in the assay chamber 541 via the inlet 571.

In the nonlimiting configuration illustrated in FIGS. 5A-5C, assay chamber 541 (which also can be considered a well) can include lower assay chamber surface 511, upper assay chamber surface (not specifically illustrated), and assay chamber sidewall(s) 531 extending between the upper and lower assay chamber surfaces. Any suitable combination of lower assay chamber surface 511, upper assay chamber surface (not specifically illustrated), assay chamber sidewall(s) 531, channel 360, lower reservoir surface (not specifically illustrated), upper reservoir surface (not specifically illustrated), and reservoir sidewall(s) 530 can be formed as discrete elements that are attached to one another or can be integrally formed with one another in a manner such as described with reference to FIGS. 3A-3B and 4A-4B, and can have any suitable shape and dimensions in a manner such as described with reference to FIGS. 1A-1B and 4C. In some variations, the device 500 can include a cover 550 and/or a bottom surface 570 as shown in FIG. 5C.

Figure 6:
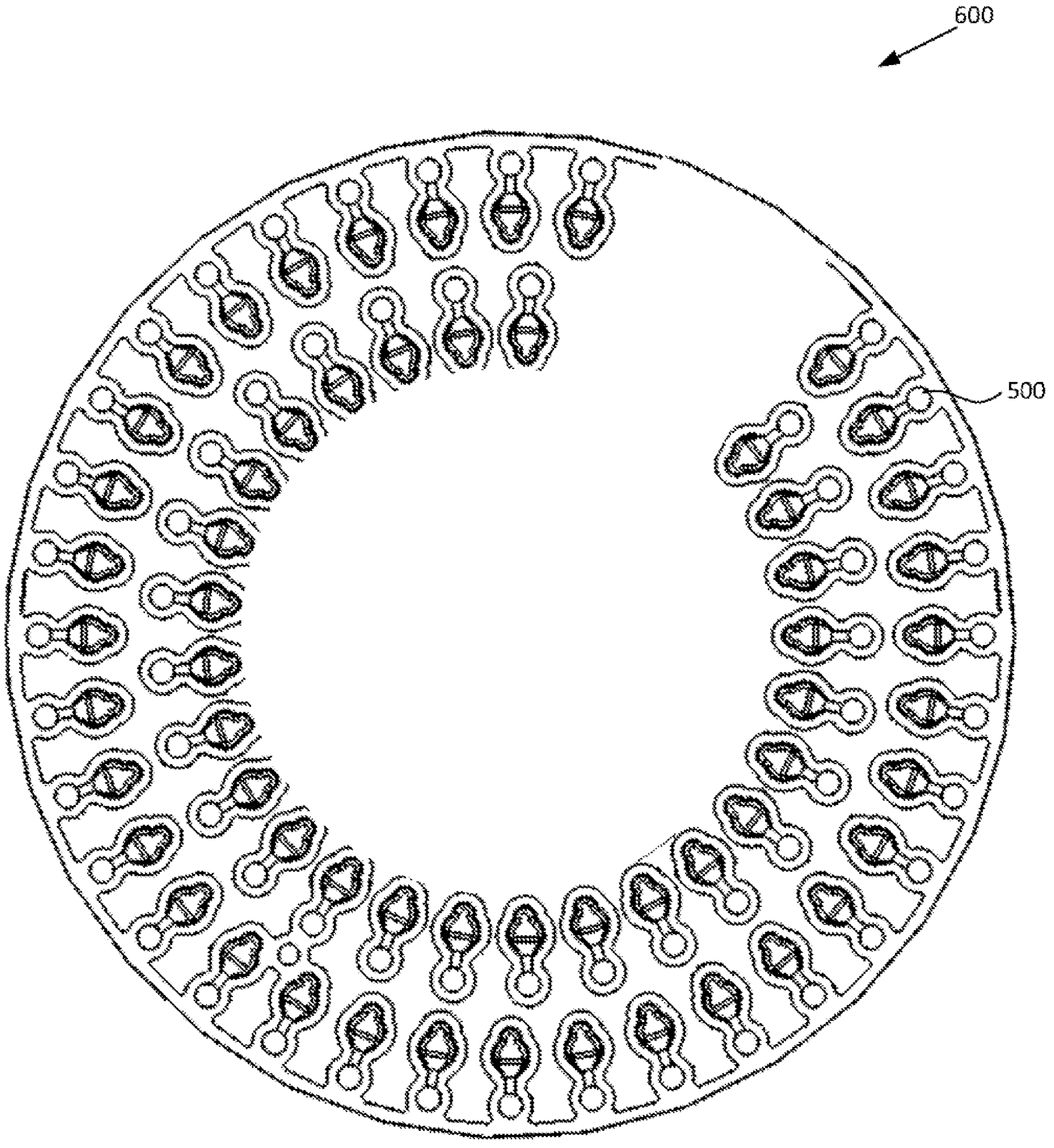
FIG. 6 schematically illustrates a plan view of a device including multiple of the devices of FIGS. 5A-5C, according to various configurations provided herein.

In the exemplary configuration illustrated in FIGS. 5A-5C, assay chamber sidewall 531 optionally includes a first portion 532 extending substantially perpendicularly to the upper and lower assay chamber surfaces. Optionally, assay chamber sidewall 531 includes a second portion 533 extending at an angle (e.g., obtuse angle, etc.) from the lower assay chamber surface 511. Responsive to application of a force such as described herein with reference to FIGS. 3A-3B, liquid that is deposited within assay chamber 541 can be conveyed upward along the second portion and into the channel. For example, FIG. 6 schematically illustrates a plan view of a device 600 including multiple of the devices 500 of FIGS. 5A-5C, according to various configurations provided herein. More specifically, devices 500 can be disposed within a rotatable disc configured so as to be centrifugally spun at a sufficient rate to transfer liquid disposed within assay chamber 541 into reservoir 540 for optical analysis.

Figure 7:
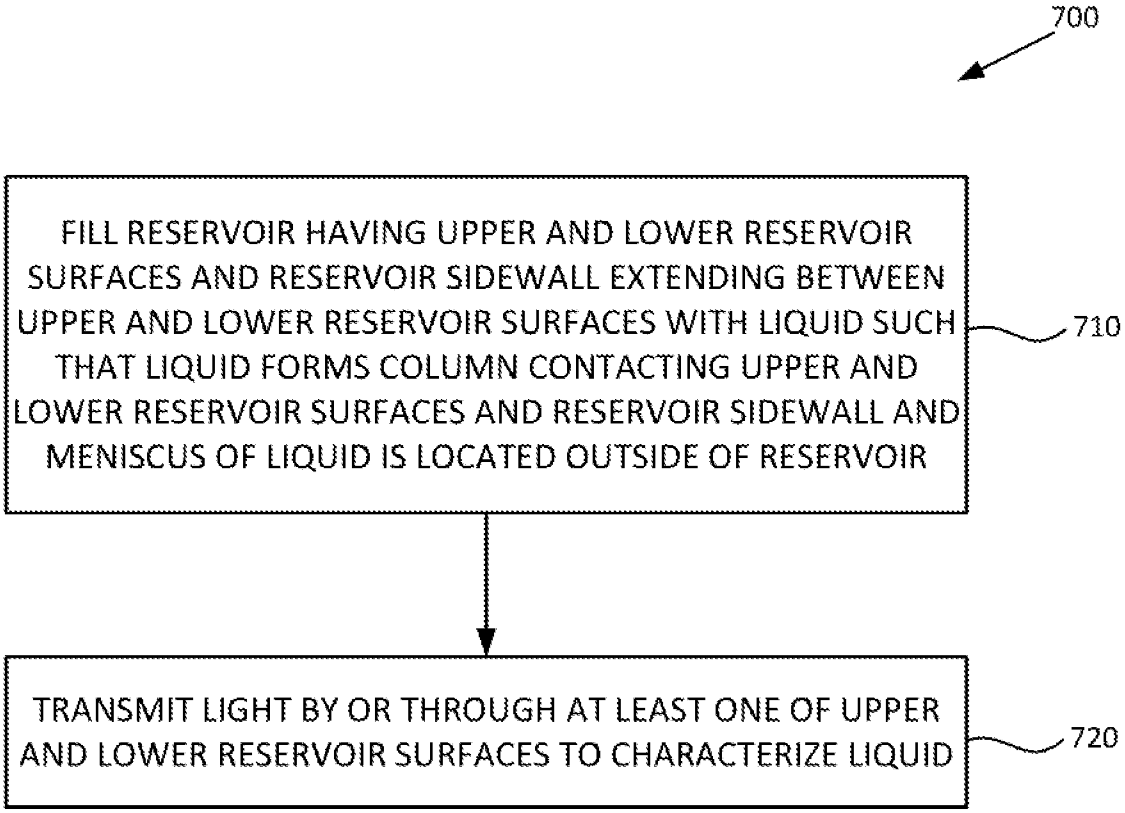
FIG. 7 illustrates an exemplary flow of operations in a method of using the devices of FIGS. 1A-6, according to various configurations provided herein.

FIG. 7 illustrates an exemplary flow of operations in a method of using the devices of FIGS. 1A-6, according to various configurations provided herein. Method 700 illustrated in FIG. 7 can include completely filling a reservoir with a liquid (710). The reservoir can include a lower reservoir surface; an upper reservoir surface; and a reservoir sidewall extending between the upper and lower reservoir surfaces, e.g., such as described with reference to FIGS. 1A-1B, 3A-3B, 4A-4C, and 5A-5C. During operation 710, the liquid forms a column contacting the upper reservoir surface, the lower reservoir surface, and the reservoir sidewall, and a meniscus of the liquid can be located outside of the reservoir, e.g., such as described with reference to FIGS. 1A-1B, 3A-3B, 4A-4C, and 5A-5C. Method 700 illustrated in FIG. 7 also can include transmitting light through at least one the upper reservoir surface and the lower reservoir surface (720), for example such as described with reference to FIGS. 2A-2B.

Optionally, the device used in method 700 can have any suitable configuration and combination of features such as described with reference to FIGS. 1A-6. For example, a channel optionally can be coupled to the reservoir sidewall. The meniscus optionally can be located within the channel. In various optional configurations, the channel and the sidewall can be integrally formed with one another, or can be discrete elements. Additionally, or alternatively, optionally the lower reservoir surface, the upper reservoir surface, and the sidewall are discrete elements attached to one another. Additionally, or alternatively, the reservoir sidewall defines a circular, rectangular, square, or irregular cross section. In various optional configurations, the reservoir has a volume of about 1-200 μL, or about 10-100 μL, or about 15-50 μL, or about 10-30 μL, or about 5-20 μL.

In some optional configurations, a well optionally can be fluidically coupled to the reservoir via the channel, wherein the meniscus optionally can be located within the well. An assay chamber optionally can be fluidically coupled to the reservoir via the channel. The assay chamber optionally can include an inlet. A reagent optionally can be within the assay chamber. Optionally, the reagent includes an antibody, enzyme, or particle.

In some configurations, method 700 optionally further includes receiving the liquid in the assay chamber via the inlet, and reacting the liquid with the reagent in the assay chamber. Additionally, method 700 optionally includes applying a force to the assay chamber, and conveying, by the channel, the liquid from the assay chamber to the reservoir responsive to application of the force. The force optionally can include a centrifugal force. For example, the reservoir optionally can be disposed in a rotatable disc, wherein applying the force includes generating the centrifugal force by rotating the disc. As another example, the force optionally can be applied via a gas.

Optionally, in the device used in method 700, the assay chamber includes a lower assay chamber surface, an upper assay chamber surface, and an assay chamber sidewall extending between the upper and lower assay chamber surfaces. The assay chamber sidewall optionally includes a first portion extending substantially perpendicularly to the upper and lower assay chamber surfaces. The assay chamber sidewall optionally includes a second portion extending at an angle (e.g., obtuse angle, etc.) from the lower assay chamber surface. Optionally, method 700 includes, responsive to application of the force, the liquid being conveyed upward along the second portion and into the channel.

Additionally, or alternatively, in the device used in method 700 the assay chamber sidewall and the reservoir sidewall optionally are integrally formed with one another. As a further option, the upper assay chamber surface and the upper reservoir surface can be integrally formed with one another and attached to the integrally formed assay chamber sidewall and the reservoir sidewall. Optionally, the lower assay chamber surface and the lower reservoir surface are integrally formed with one another and attached to the integrally formed assay chamber sidewall and the reservoir sidewall. In various optional configurations of the device used in method 700, the assay chamber sidewall, the channel, and the reservoir sidewall can be integrally formed with one another. In various optional configurations of the device used in method 700, the assay chamber sidewall and the reservoir sidewall can be discrete elements. In various optional configurations of the device used in method 700, the upper assay chamber surface and the upper reservoir surface can be discrete elements. In various optional configurations of the device used in method 700, the lower assay chamber surface and the lower reservoir surface can be discrete elements. In various optional configurations of the device used in method 700, the assay chamber sidewall, the channel, and the reservoir sidewall can be discrete elements.

Optionally, method 700 includes generating the light of operation 720. Optionally, the light can be generated by a laser, light emitting diode, or lamp. Optionally, method 700 includes transmitting the light into the column through the upper reservoir surface. As a further option, method 700 further can include transmitting the light through the column and then through the lower reservoir surface. Alternatively, method 700 optionally can include transmitting the light into the column through the lower reservoir surface. As a further option, method 700 can include transmitting the light through the column and then through the upper reservoir surface.

Additionally, or alternatively, method 700 further can include receiving, by a sensor, the light transmitted through the at least one of the upper reservoir surface and the lower reservoir surface. For example, the sensor optionally receives the light through the upper reservoir surface. As another example, the sensor optionally receives the light through the lower reservoir surface. Additionally, or alternatively, optionally the light is generated by fluorescence or chemiluminescence Note that devices such as described herein with reference to FIGS. 1A-6 and methods such as described herein with reference to FIG. 7 suitably can be used to read out information from any type of liquid. One nonlimiting example of a liquid is a bodily fluid, such as whole blood, blood plasma, blood cells, urine, or spit. Other nonlimiting examples of a liquid include a food sample or a water sample. In yet another example, the liquid can include a purified nucleic acid. In still another example, the liquid can include a pharmaceutical compound. Additionally, or alternatively, the liquid can include a buffer or reagent. Such buffer or reagent optionally can be mixed with one or more other liquids such as exemplified herein. In one specific, nonlimiting example, the liquid includes blood plasma which is mixed with a buffer and with a reagent within an assay chamber such as described herein with reference to FIG. 3A-3B, 4A, or 5A-5C prior to using centrifugal force to move the mixture into a read well for optical analysis.

The present devices can be constructed using any suitable materials or combination of materials, such as any suitable combination of polymer, glass, metal, and semiconductor. Additionally, the present devices can be constructed using any suitable fabrication technique(s), such as molding, 3D printing, machining, laminate assemblies, thermoforming, chemical or laser etching, casting, and/or hot embossing.

It will be appreciated that the current subject matter provides many advantages. For example, the designs provided herein can limit the rate of evaporation by restricting the surface area of the fluid that is in contact with air. In particular, the current designs can constrict the air interface (meniscus) to the channel or to another area outside the reservoir such as the well.

As another example, the liquid reservoir designs provided herein can limit the movement of beads (used to capture analytes such as small molecules, proteins, nucleic acids, etc.) in solution when the reservoir is filled with fluid. Such an arrangement is advantageous for imaging purposes as it is desirable for the beads to not move during the imaging process. Beads in solution in the read chamber will settle over time to partially cover the bottom surface of the reservoir. Given that the bead solution is incompressible, and there is no head room in the reservoir, the fluid and beads in solution do not substantially move when the liquid reservoir is spun (i.e., by centrifugal force, etc.) or is otherwise agitated. This arrangement allows for beads in solution within the reservoir to be effectively imaged even when a device including such reservoir (e.g., disc-shaped cassette, etc.) is in motion.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed:

1. A method to optically characterize a sample, the method comprising:

a. loading a sample into a sample analysis apparatus, the apparatus comprising:

a rotatable disc having a plurality of devices each of the plurality of devices consisting of an optically readable reservoir, a load chamber and a channel, the optically readable reservoir comprising of a lower optically readable reservoir surface, the lower optically readable reservoir surface at least partially optically transparent the lower optically readable reservoir surface without an inlet and without a vent;

an upper optically readable reservoir surface, the upper optically readable reservoir surface at least partially optically transparent, the upper optically readable reservoir surface without an inlet and without a vent; and a first optically readable reservoir sidewall and a second optically readable reservoir sidewall extending between the upper and lower optically readable reservoir surfaces, the first optically readable reservoir sidewall comprising an opening, wherein:

the lower optically readable reservoir surface, the upper optically readable reservoir surface, and the first and second optically readable reservoir sidewalls define the optically readable reservoir having a height, a width, and a volume of about 1-200 μL, the optically readable reservoir having a width greater than a height of the optically readable reservoir, the optically readable reservoir is configured to be completely filled by a liquid such that the liquid forms a column contacting the upper optically readable reservoir surface, the lower optically readable reservoir surface, and the first and second optically readable reservoir sidewalls; and the load chamber having a lower load chamber surface, an upper load chamber surface, a first sidewall and a second sidewall each extending between the upper and lower load chamber surfaces, wherein the first sidewall is perpendicular to the upper load chamber surface and the second sidewall extends at an obtuse angle with respect to the lower load chamber surface;

an inlet disposed in the upper load chamber surface; and the channel having a lower channel surface extending from the lower load chamber surface and terminating at the first optically readable reservoir sidewall opening, and an upper channel surface coextensive with the upper optically readable reservoir surface and the upper load chamber surface, wherein the channel has a width and a volume that is less than the width and the volume of the optically readable reservoir, and the volume of the channel being sized to provide a capillary action forming a meniscus of the liquid outside of the optically readable reservoir and within the channel; wherein the channel serves as the sole sample ingress and egress for the optically readable reservoir;

b. moving, by spinning the sample analysis apparatus, sample from the load chamber by directing the sample upward along the second sidewall and through the channel connecting the load chamber and the optically readable reservoir;

c. filling completely the optically readable reservoir with the sample by spinning the sample analysis apparatus, the sample forming a continuous liquid column extending from the lower optically readable reservoir surface to the upper optically readable reservoir surface;

d. forming, by spinning the sample analysis apparatus, the meniscus of the sample outside of the optically readable reservoir and within the channel, the meniscus positioned between the first optically readable reservoir sidewall opening and the load chamber; and e. transmitting light through at least the transparent upper optically readable reservoir surface of the optically readable reservoir thereby characterizing the sample in the optically readable reservoir.

2. The method of claim 1, wherein the light is not transmitted through the meniscus of the sample.

3. The method of claim 1, wherein the load chamber is made of a non-transparent material.

4. The method of claim 1, further comprising transmitting light through the lower optically readable reservoir surface of the optically readable reservoir.

5. The method of claim 1, wherein a light source is positioned over the transparent upper optically readable reservoir surface of the optically readable reservoir and configured to transmit the light through the transparent upper optically readable reservoir surface.

6. The method of claim 1, further comprising receiving by a sensor the light transmitted through the transparent upper optically readable reservoir surface.

7. The method of claim 1, wherein the load chamber comprises a dry reagent within the load chamber prior to moving the sample from the load chamber to the optically readable reservoir.

8. The method of claim 7, further comprising dissolving a dry reagent in the sample within the load chamber prior to moving the sample to the optically readable reservoir.

9. The method of claim 1, further comprising transmitting, by a light source positioned over the upper optically readable reservoir surface of the optically readable reservoir and configured to transmit light through the upper optically readable reservoir surface, through the continuous liquid column within the optically readable reservoir, and then through the lower optically readable reservoir surface, and receiving, by a sensor positioned under the lower optically readable reservoir surface, the light through the lower optically readable reservoir surface, thereby characterizing the sample in the optically readable reservoir.

10. The method of claim 1, wherein the load chamber has a width less than a height of the load chamber.

11. The method of claim 1, wherein the meniscus formed in the channel has a surface area smaller than a surface area of the lower optically readable reservoir surface, thereby reducing evaporation of the sample.

12. The method of claim 1, wherein step (e) further comprises receiving, by a sensor positioned under the lower optically readable reservoir surface, the light transmitted through the lower optically readable reservoir surface.

13. The method of claim 1, wherein step (c) further comprises limiting movement of particles in the sample within the optically readable reservoir when the sample analysis apparatus is spinning, the particles being captured against the lower optically readable reservoir surface.

14. A method to optically characterize a sample, the method comprising:

a. loading a sample into a sample analysis apparatus, the sample analysis apparatus consisting of a channel, a load reservoir and an optically readable reservoir, the load reservoir comprising a load reservoir upper surface made of a non-transparent material, the optically readable reservoir comprising optically transparent upper optically readable reservoir surface made of a second optically transparent material, the upper optically readable reservoir surface of the optically readable reservoir without an inlet and without a vent;

b. moving by spinning the sample analysis apparatus the sample out of the load reservoir;

c. filling by spinning the sample analysis apparatus the optically readable reservoir with the sample;

d. forming a liquid column from the sample that contacts the upper surface of the optically readable reservoir, a lower optically readable reservoir surface, a first optically readable reservoir sidewall, and a second optically readable reservoir sidewall wherein the lower optically readable reservoir surface without an inlet and without a vent;

e. filling the channel partially by spinning the sample analysis apparatus;

f. forming a meniscus of the sample in the channel by spinning the sample analysis apparatus;

g. transmitting light through at least the transparent upper surface of the optically readable reservoir thereby characterizing the sample in the optically readable reservoir.

15. A method to optically characterize a sample, the method comprising:

a. loading a sample into a sample analysis apparatus, the apparatus comprising:

a rotatable disc having a plurality of devices arranged in multiple concentric circles, each of the plurality of devices consisting of an optically readable reservoir, a load chamber and a channel;

the optically readable reservoir comprising a lower optically readable reservoir surface, the lower optically readable reservoir surface at least partially optically transparent the lower optically readable reservoir surface without an inlet and without a vent;

an upper optically readable reservoir surface, the upper optically readable reservoir surface at least partially optically transparent, the upper optically readable reservoir surface without an inlet and without a vent; and a first and second optically readable reservoir sidewalls extending between and connecting the upper and lower optically readable reservoir surfaces, wherein:

the lower optically readable reservoir surface, the upper optically readable reservoir surface, and the first and second optically readable reservoir sidewalls define the optically readable reservoir having a height, a width, and a volume of about 1-200 μL, the first optically readable reservoir sidewall comprising an opening, and the optically readable reservoir is configured to be completely filled by a liquid such that the liquid forms a column contacting the upper optically readable reservoir surface, the lower optically readable reservoir surface, and the first and second optically readable reservoir sidewalls; and the load chamber having a lower load chamber surface, an upper load chamber surface, and a load chamber sidewall extending between the upper and lower load chamber surfaces, wherein the lower load chamber surface has a first portion extending substantially parallel to the upper load chamber surface and a second portion extending at an obtuse angle with respect to the first portion and an inlet disposed in the upper load chamber surface; and the channel having a lower channel surface extending from the second portion of the lower load chamber surface and terminating at the first optically readable reservoir sidewall opening, and an upper channel surface coextensive with the upper optically readable reservoir surface and the upper load chamber surface, wherein the channel has a width and a volume that is less than the width and the volume of the optically readable reservoir, and the volume of the channel being sized to provide a capillary action forming a meniscus of the liquid outside of the optically readable reservoir and within the channel, wherein the channel serves as the sole sample ingress and egress for the optically readable reservoir;

b. moving by spinning the sample analysis apparatus a portion of the sample from the load chamber upward along the second portion of the load chamber and into the channel connecting the load chamber and the optically readable reservoir;

c. moving by spinning the sample analysis apparatus a portion of the sample from the channel through the opening in the first optically readable reservoir sidewall into the optically readable reservoir;

d. continuing spinning the sample analysis apparatus to completely fill the optically readable reservoir with the liquid while maintaining the meniscus of the sample outside of the optically readable reservoir and within the channel;

e. transmitting light through at least the transparent upper optically readable reservoir surface of the optically readable reservoir thereby characterizing the sample in the optically readable reservoir.

* * * * *